Figure 1:
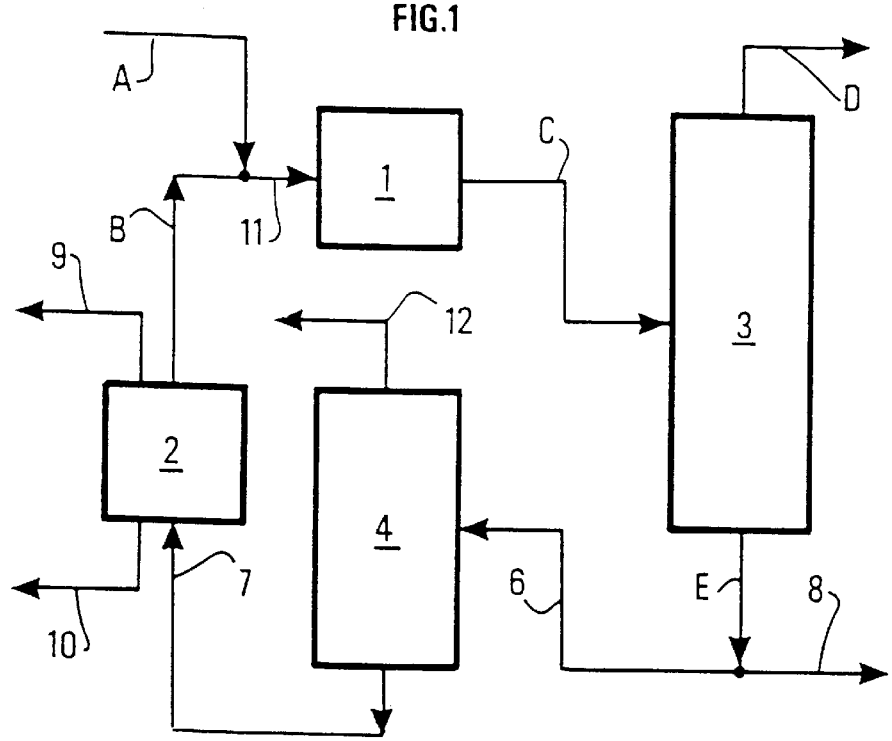

United States Patent
Dorbon et al.

[11] Patent Number: 5,969,203
[45] Date of Patent: *Oct. 19, 1999

[54] PROCESS FOR THE PRODUCTION OF HIGH PURITY ISOBUTENE COMBINING REACTIVE DISTILLATION WITH HYDROISOMERIZATION, DISTILLATION AND SKELETAL ISOMERIZATION

[75] Inventors: Michel Dorbon, Lyons; Jean-Alain Chodorge, Antony; Jean Cosyns, Maule; Jean-Charles Viltard, Valence; Blaise Didillon, Rueil Malmaison, all of France

[73] Assignee: Institut Francais du Petrole, Rueil Malmaison, France

[*] Notice: This patent is subject to a terminal disclaimer.

[21] Appl. No.: 08/996,122

[22] Filed: Dec. 22, 1997

[30] Foreign Application Priority Data

Dec. 23, 1996 [FR] France ................................. 96 16022

[51] Int. Cl.$^6$ ................................. C07C 1/00; C07C 5/22
[52] U.S. Cl. ..................... 585/324; 585/671; 585/351; 203/DIG. 6
[58] Field of Search ................................. 585/671, 351, 585/324; 203/DIG. 6

[56] References Cited

U.S. PATENT DOCUMENTS

| | | | |
|---|---|---|---|
| 4,104,321 | 8/1978 | Ward | 260/677 A |
| 4,236,027 | 11/1980 | Al-Chalabi | 585/670 |
| 4,255,605 | 3/1981 | Dixon | 585/332 |
| 5,621,150 | 4/1997 | Rastelli et al. | 568/697 |
| 5,689,015 | 11/1997 | Hunt et al. | 568/697 |

FOREIGN PATENT DOCUMENTS 2130387 11/1972 France.

OTHER PUBLICATIONS

Patent Abstracts of Japan, vol. 10, No. 166 (C–353), Jun. 13, 1986, (JP 61–018732A, Mitsui Sekiku Kagaku Kogyo), Jan. 27, 1986.
Patent Abstracts of Japan, vol. 13, No. 260 (C–607), Jun. 15, 1989, (JP 01–061434A, Tonen Sekiyukagaku), Mar. 8, 1989.

*Primary Examiner*—Glenn Caldarola
*Assistant Examiner*—Tam M. Nguyen
*Attorney, Agent, or Firm*—Millen, White, Zelano, & Branigan, P.C.

[57] ABSTRACT

The invention relates to a process for producing high purity isobutene from a hydrocarbon cut essentially comprising olefinic hydrocarbons containing 4 carbon atoms per molecule including isobutene, also butene-1 and butene-2 compounds in a ratio which substantially corresponds to the thermodynamic equilibrium. The process comprises passing the cut into a distillation zone (3) associated with a hydroisomerization reaction zone, the bottom product of the distillation zone comprising butene-2 compoundw being passed into a second distillation zone (4), preferably an extractive distillation zone, to obtain a first effluent comprising butene-2 compounds as its major portion and a second effluent comprising normal-butane as its major portion, the major portion of the first effluent being passed into a skeletal isomerization zone (2) where the linear butenes are at least partially isomerized to isobutene, at least part of the principal effluent from the skeletal isomerization zone being recycled upstream of the reactive distillation zone (1).

15 Claims, 1 Drawing Sheet

5,969,203

PROCESS FOR THE PRODUCTION OF HIGH PURITY ISOBUTENE COMBINING REACTIVE DISTILLATION WITH HYDROISOMERIZATION, DISTILLATION AND SKELETAL ISOMERIZATION

FIELD OF THE INVENTION

The invention relates to a process for producing high purity isobutene from a hydrocarbon cut essentially comprising olefinic hydrocarbons containing 4 carbon atoms per molecule including isobutene, also butene-1 and butene-2 compounds in a ratio which substantially corresponds to the thermodynamic equilibrium, the process comprising passing the cut into a distillation zone associated with a hydroisomerisation reaction zone, the bottom product of the distillation zone comprising butene-2 compounds being passed into a second distillation zone, preferably an extractive distillation zone, to obtain an effluent comprising butene-2 compounds as its major portion, the major portion of which is passed into a skeletal isomerisation zone where the linear butenes are at least partially isomerised to isobutene, at least part of the principal effluent from the skeletal isomerisation zone being recycled upstream of the reactive distillation zone.

BACKGROUND OF THE INVENTION

Isobutene for polymerisation must be more than 99% pure and can contain only traces of butene-1 and butene-2 compounds (several tens of parts per million, ppm). If the degree of impurities in the isobutene is too high, the quality of the polymers obtained is poorer and the polymerisation yield is lower. The other olefinic hydrocarbons containing 4 carbon atoms per molecule must therefore be eliminated from a hydrocarbon cut containing isobutene. Since the boiling points of butene-1 and isobutene are very close, it is not possible to separate them by distillation unless considerable means are used. The other olefinic hydrocarbons containing 4 carbon atoms can be separated from the isobutene by distillation.

The principal problem in the production of high purity isobutene is thus separating butene-1 from isobutene. A number of routes can be used to carry out this separation.

The first route consists of extracting using sulphuric acid: isobutene is selectively hydrated and then regenerated by treating the aqueous phase. If the temperature and concentration are properly controlled, this process can produce high purity isobutene. However, the yield normally does not exceed 90% as extraction is not complete and dimers and oligomers are formed, leading to the formation of toxic acid mud.

The second route consists of cracking methyl tertio-butyl ether (MTBE): isobutene is extracted from the $C_4$ cut by reacting it with methanol to form MTBE. The MTBE is thus cracked to methanol and isobutene using an acid catalyst. The yield on recovery can be at least 96%. The isobutene produced is of high purity but it has to be freed of the dimethylether which can form during cracking.

The third possible route is dehydration of tertiary-butyl alcohol (TBA). In the previous operation, methanol can be replaced by water, leading to the production of TBA. The isobutene is then recovered by dehydrating the TBA. This route is not used in practice, mainly because TBA is closely linked to the propylene oxide market. TBA can be a by-product of propylene oxide from those processes.

The butene-1-isobutene separation problem has existed for a long time. A variety of solutions have been proposed but none is completely satisfactory in terms of efficiency of separation without the appearance of by-product(s). U.S. Pat. No. 2,403,672 describes a process for separating isobutene from an isobutene-butene-1 mixture which comprises introducing the mixture into an isomerisation zone and fractionating it, wherein the isomerisation catalyst also acts as a packing to allow distillation. This solution has the major disadvantage of not being very efficient in distillation and thus has a mediocre capacity for separating isobutene from butene-1.

SUMMARY OF THE INVENTION

The process of the invention can produce high purity isobutene, at low cost and in a high yield, from an olefinic $C_4$ cut containing at least isobutene, as well as butene-1 and butene-2 compounds, in a ratio which substantially corresponds to the thermodynamic equilibrium, the cut generally originating from a steam cracking process, such as a crude $C_4$ cut or 1-raffinate (obtained after extracting butadiene from the crude $C_4$ cut), or from catalytic cracking. The process of the invention is characterized in that the operations of distillation, hydroisomerisation and skeletal isomerisation of the linear butenes to isobutene are integrated, and arranged and operated to minimise the investment costs of the process, to maximise conversion of butene-1 to butene-2 compounds, to minimise hydrogenation of isobutene to isobutane and to transform a portion of the linear butenes to isobutene in order to maximise the isobutene yield. Thus the process of the invention can effect at least partial selective hydrogenation of polyunsaturated compounds which are usually dienes or acetylenes such as butadiene, vinylacetylene, methylacetylene and ethylacetylene, when these compounds are present in the feed, hydroisomerisation of butene-1 to butene-2 compounds (cis and trans), and skeletal isomerisation of linear butenes to isobutene. The butene-2 compounds produced from this hydrogenation and hydroisomerisation can then be separated from the isobutene by distillation, which is not the case with butene-1. The bottom product from the reactive distillation zone, which contains mainly butene-2 compounds and generally normal-butane, passes into a second distillation zone, preferably an extractive distillation zone, to better remove the alkanes which are impurities, then into a skeletal isomerisation unit where at least part of the linear butenes is transformed into isobutene; the products from this skeletal isomerisation are recycled upstream of the reactive distillation step, for example mixed with the feed from the reactive distillation zone, in order to separate the isobutene produced from the linear butenes. Compared with the other processes cited above, the process of the invention has the advantage of having a very high isobutene yield which is generally over 100% if linear butenes are present in the feed. When the feed is a $C_4$ cut from a steam cracking unit from which the major portion of the butadiene has been extracted, i.e. a 1-raffinate, the yields are generally over 120%.

The process of the invention is a process for treating a feed, the major portion comprising olefinic hydrocarbons containing 4 carbon atoms per molecule, including isobutene, also butene-1 and butene-2 compounds in a ratio which substantially corresponds to the thermodynamic equilibrium, in which the feed is treated in a distillation zone, generally comprising a stripping zone and a rectification zone, associated with a hydroisomerisation reaction zone, so as to ensure continuity of distillation and to produce an overhead effluent from the distillation zone which is rich in isobutene, generally of high purity, and a bottom effluent from the distillation zone which is rich in butene-2 compounds, the major portion of the bottom effluent being sent to a second distillation zone, preferably an extractive zone, to obtain a first effluent comprising butene-2 compounds as its major portion and a second effluent comprising normal-butane as its major portion, the major portion of the first effluent being passed into a skeletal isomerisation zone, and the effluent from the skeletal isomerisation zone being recycled upstream of the distillation zone (with respect to the general direction of circulation of effluent in the process). The process can produce high purity isobutene.

The feed which supplies the distillation zone is generally introduced into the zone at at least one level in the zone, preferably principally at a single level in the zone. The ratio of butene-1 to butene-2 compounds on introduction substantially corresponds to the thermodynamic equilibrium. In a preferred implementation of the process of the invention, the feed is obtained from a cut comprising mainly olefinic hydrocarbons containing 4 carbon atoms per molecule, by treating the cut in a first hydroisomerisation zone, which is generally independent of the optional external portion of the hydroisomerisation reaction zone associated with the distillation zone, the major portion of the effluent from the first hydroisomerisation zone thus acting as a feed, a principal or secondary feed as will be defined below, which supplies the distillation zone. In such a case a portion, preferably the major portion, of the effluent from the skeletal isomerisation zone recycled upstream of the distillation zone is preferably recycled upstream of the first hydroisomerisation zone. If the feed comprises polyunsaturated compounds, generally dienes and/or acetylene compounds, these compounds are preferably transformed into butenes in the first hydroisomerisation zone before introducing it into the distillation zone.

Any other technique which can produce a feed in which the butene-1 and butene-2 compounds are in a ratio which substantially corresponds to the thermodynamic equilibrium from a cut containing $C_4$ olefinic hydrocarbons including butene-1 and isobutene as its major portion can also be used in the process of the invention.

The first optional hydroisomerisation reaction zone, located upstream of the distillation-reaction zone, carries out at least partial selective hydrogenation of polyunsaturated compounds, usually dienes such as butadiene, also hydroisomerisation of at least a portion of the butene-1 to butene-2 compounds. It generally comprises at least one catalytic hydroisomerisation bed comprising a hydroisomerisation catalyst, preferably 1 to 4 catalytic bed(s); when at least two catalytic beds are incorporated in the reaction zone, these two beds are preferably located in at least two reactors, in series or in parallel, preferably in series. As an example, the first reaction zone can comprise a single reactor containing at least one catalytic bed, preferably a single catalytic bed. In a preferred implementation of the process of the present invention, the first reaction zone comprises two reactors which are generally in series each comprising one catalytic bed, preferably a single catalytic bed. When the reaction zone comprises at least two reactors, optional recycling of at least a portion of the effluent from at least one of the reactors in the first reaction zone to the first zone is generally to the inlet to a reactor, preferably the reactor, preferably before injection of a gaseous compound containing hydrogen. The recycle can be around the first zone per se, i.e., generally to the inlet to the first reactor of the zone, preferably before injection of a gaseous compound containing hydrogen; as an example, in the case of two reactors, at least a portion of the effluent from the second reactor can be recycled to the inlet to the first reactor. This can advantageously reduce the amount of polyunsaturated compounds in the effluent from the first reaction zone.

The operating conditions of the first hydroisomerisation zone, when present, are generally as follows: the catalyst is identical to the catalyst in the hydroisomerisation zone which is described below. The pressure is generally in the range 4 to 40 bar (1 bar=0.1 MPa), preferably in the range 6 to 30 bar. The temperature is generally in the range 100° C. to 150° C., preferably in the range 20° C. to 100° C. The $H_2$/hydrocarbons molar ratio is generally adjusted so as to obtain practically complete conversion of the polyunsaturated compounds such as butadiene and sufficient isomerisation of butene-1 to butene-2 compounds with limited alkane formation.

The hydroisomerisation reaction zone associated with the distillation zone generally comprises at least one catalytic hydroisomerisation bed comprising a hydroisomerisation catalyst, preferably 2 to 6 beds, and more preferably 2 to 4 catalytic beds; when at least two catalytic beds are incorporated in the distillation zone, these two beds are preferably separated by at least one distillation contact means. The hydroisomerisation reaction zone at least partially hydroisomerises at least a portion, preferably the major portion, of the butene-1 present in the feed to butene-2 compounds (cis and trans), generally such that the butene-1 content of the overhead effluent from the distillation zone is maximally equal to a certain level.

The hydroisomerisation reaction zone associated with the distillation zone at least partially hydroisomerises the butene-1 present in the liquid phase (reflux) flowing at the draw-off level in the distillation zone. It is either completely internal to the distillation zone, or completely external of the distillation zone, or both internal to and external of the distillation zone.

In a preferred implementation of the process of the invention, in addition to supplying a principal feed to the distillation zone, it is also supplied with a secondary feed (with respect to the principal feed) which may or may not originate from a hydroisomerisation reaction zone such as the first optional hydroisomerisation reaction zone, independently or otherwise of the supply of principal feed to the distillation zone. The secondary feed is generally a $C_4$ cut containing at least isobutene, also butene-1 and butene-2 compounds, in a ratio corresponding substantially to the thermodynamic equilibrium, and generally originates from a steam cracking process, such as a crude $C_4$ cut or 1-raffinate, or from catalytic cracking; generally and preferably, the secondary feed is a $C_4$ cut which is essentially free of polyunsaturated compounds and its butene-1 content is lower than the butene-1 content in the principal feed. If the amount of unsaturated compounds in the secondary feed is high, the feed is preferably treated in a selective hydrogenation zone before it enters the distillation zone.

When the principal feed is introduced at a single introduction level, the secondary feed is generally introduced into the distillation zone at at least one introduction level, preferably at a single introduction level, the introduction level depending on the composition of the secondary feed. Thus in a first example, the secondary feed can be very rich in isobutene and contain at least 1.5 times the butene-1 contained in the principal feed, in which case the secondary feed is preferably introduced at a single level generally located above the principal feed introduction level. In a second example, the secondary feed can be practically free of butene-1, in which case the secondary feed is preferably introduced at a single level generally located below the principal feed introduction level. It is also possible to mix the principal feed and the secondary feed before introduction into the distillation zone.

The distillation zone generally comprises at least one column provided with at least one distillation contact means selected from the group formed by simple plates, multi-downcomer plates, bulk packing and structured packing, as are known to the skilled person, such that the overall efficiency is at least five theoretical plates. In cases which are known to the skilled person where using a single column causes problems, the zone is preferably separated so as to use at least two columns which are placed end to end to form the zone, i.e., the rectification, optional reaction zone and stripping zone are distributed over the columns. In practice, when the reaction zone is at least partially internal to the distillation zone, the rectification zone or the stripping zone, preferably the stripping zone, is generally located in at least one column which is different from the column comprising the internal portion of the reaction zone.

In a first implementation of the process of the invention, the hydroisomerisation reaction zone associated with the distillation zone is at least partially external to the distillation zone. In general, the process of the invention comprises 1 to 6, preferably 2 to 4, draw-off level(s) which supply the external portion of the hydroisomerisation zone. In such a case, the liquid to be hydroisomerised circulates, either partially or completely, firstly in the external portion of the hydroisomerisation zone then in the internal portion of the zone. Two cases are thus possible. In the first case, the external portion of the hydroisomerisation zone is supplied by a single draw-off level, and thus if that portion comprises more than two reactors, these are located in series or in parallel. In the second case, which is preferred, the external portion of the hydroisomerisation zone is supplied by at least two draw-off levels. A portion of the external portion of the hydroisomerisation zone which is supplied by a given draw-off level, if that external portion comprises at least two draw-off levels, generally comprises at least one reactor, preferably a single reactor. If that portion of the external portion comprises at least two reactors, each reactor external to the distillation zone is supplied by a single draw-off level, preferably associated with a single re-introduction level, the draw-off level being distinct from the draw-off level which supplies the other reactor(s).

The process of the invention is generally such that the feed in all parts of the hydroisomerisation reaction zone, whether it is internal or possibly external, is drawn off from one draw-off level and represents at least a portion, preferably the major portion, of the liquid (reflux) flowing in the distillation zone, preferably flowing in the rectification zone and more preferably flowing at an intermediate level in the rectification zone, at least a portion, preferably the major portion, of the effluent from the hydroisomerisation reaction zone being re-introduced into the distillation zone so as to ensure continuity of distillation.

In the first implementation, the process of the invention can isomerise a large proportion of the butene-1 to butene-2 compounds external the distillation zone, possibly under pressure and/or temperature conditions which are different to those used in the column. The inlet temperature (or outlet temperature respectively) at the draw-off level which supplies the catalytic bed of the portion of the hydroisomerisation zone located external to the column is preferably similar, i.e., the difference is substantially less than 10° C., to the temperature at the height of the draw-off level (respectively the re-introduction level). Similarly, the hydroisomerisation reaction can advantageously be carried out in the portion of the reaction zone which is located external to the column, at a pressure which is higher than that used inside the distillation zone. This pressure increase can also increase the amount of the gaseous stream containing hydrogen which dissolves in the liquid phase containing the butene-1 to be isomerised.

In the portion of the hydroisomerisation zone associated with the distillation zone which is external to the distillation zone, the operating conditions are generally independent of the operating conditions of the distillation zone. They are generally as follows. The pressure required for this hydroisomerisation step is generally about 1 to 40 bars absolute, preferably about 2 to 30 bars, and more preferably about 4 to 25 bars. The operating temperature in the hydroisomerisation zone is generally about 20° C. to about 150° C., preferably about 40° C. to 100° C., and more preferably about 40° C. to 80° C. The space velocity in the hydroisomerisation zone, calculated with respect to the catalyst, is generally about 1 to 1 to 100 $h^{-1}$, more particularly about 4 to 50 $h^{-1}$ (volume of feed per volume of catalyst per hour). The corresponding hydrogen flow rate is such that the molar ratio of $H_2$/hydrocarbons entering the hydroisomerisation zone is preferably at least $10^{-5}$. This ratio is usually about $10^{-5}$ to about 3, normally about $10^{-4}$ to about 1. The catalyst in this portion of the hydroisomerisation zone external to the distillation zone is disposed using any technology which is known to the skilled person.

In order to carry out the hydroisomerisation of the process of the invention, the theoretical molar ratio of hydrogen required for the desired conversion of butene-1 is such that the molar ratio of $H_2$/hydrocarbons entering the reaction zone associated with the distillation zone is at least $10^{-5}$. This molar ratio can be optimised so that all the hydrogen is consumed in the hydroisomerisation reactions to avoid the need for a hydrogen recovery apparatus at the outlet from the reaction zone, and to minimise side reactions in which the isobutene is hydrogenated to maximise the isobutene yield from the process, and finally so that there is sufficient hydrogen throughout the length of the reaction zone so that hydroisomerisation of butene-1 to butene-2 compounds can occur. However, if the conditions are such that there is an excess of hydrogen, the excess hydrogen can advantageously be recovered using one of the techniques which are described below, for example. As an example, the excess hydrogen which leaves the distillation zone overhead is recovered then injected upstream of the compression stages associated with a catalytic reforming unit, mixed with hydrogen from that unit, the unit preferably operating at low pressure (i.e., generally at a pressure of less than 8 bars). This excess hydrogen can also be recovered then compressed and re-used in the reaction zone.

For the first implementation, the process of the invention includes the use of a pumparound technique, i.e., pumping in a closed circuit, consisting of passing a portion, preferably the major portion, of the liquid (reflux) outside the distillation zone, by a factor which is preferably in the range 0.5 to 1.5, more preferably in the range 0.75 to 1.3, i.e., the flow rate of a catalytic bed in the external portion of the hydroisomerisation zone associated with the distillation zone, the bed being supplied at a draw-off level with at least a portion of the liquid effluent (reflux) flowing on a distillation plate associated with the draw-off level (i.e., from which that portion of the liquid effluent is drawn off) and by at least a portion of the liquid corresponding to recycling the effluent from the bed just above or just below or substantially at the same height as the draw-off level, is less than or greater than the flow rate of the liquid flowing on the plate, more preferably equal to the flow rate of the liquid flowing on the plate, i.e., generally of the same order of magnitude as the flow rate of the liquid flowing on the plate.

In one embodiment of the first implementation of the process of the invention, the hydroisomerisation zone is both partially incorporated into the distillation zone, i.e., internal to the distillation zone, and partially external of the distillation zone. In such an embodiment, the hydroisomerisation zone comprises at least two catalytic beds, preferably at least three catalytic beds, at least one catalytic bed being internal to the distillation zone, and at least one catalytic bed being external of the distillation zone. For the optional portion of the reaction zone which is external of the distillation zone, re-introduction of the effluent to the distillation zone is substantially proximate, i.e., generally substantially at the same height or just above or just below, normally substantially at the same height or just above, i.e., located at a distance corresponding to a height in the range 0 to 4 theoretical plates from a draw-off level, preferably from said draw-off level, to ensure continuity of distillation. For the portion of the reaction zone which is internal to the distillation zone, liquid (reflux) is drawn off naturally by flow into the portion of the reaction zone which is internal to the distillation zone, and re-introduction of the liquid to the distillation zone is also natural by flow of liquid from the portion of the reaction zone internal to the distillation zone. Further, the process of the invention is preferably such that the flow of liquid containing the reactant, butene-1, is co-current or counter-current to the flow of the gaseous stream containing hydrogen, for each catalytic bed in the portion internal to the hydroisomerisation zone contained in the distillation zone.

In a further preferred embodiment of the first implementation of the process of the invention, independently of the preceding embodiment, the hydroisomerisation zone is completely external of the distillation zone. It thus has the characteristics of the external portion of the hydroisomerisation zone in the preceding embodiment.

The major portion, preferably almost all, of the hydrogen in the gaseous stream used in the process of the invention for hydroisomerising butene-1 to butene-2 compounds, whether in the first optional hydroisomerisation zone or in the hydroisomerisation zone associated with the distillation zone, originates from outside the distillation zone. It may originate from any source which produces hydrogen which is at least 50% by volume pure, preferably at least 80% by volume pure, and more preferably at least 90% by volume pure. As an example, hydrogen originating from steam cracking processes, catalytic reforming processes, PSA (pressure swing adsorption) processes or from electrochemical generation processes can be used.

When at least part of the hydroisomerisation zone associated with the distillation zone is incorporated in the distillation zone, the hydroisomerisation catalyst can be disposed in that incorporated part using different technologies for carrying out catalytic distillation. They are essentially of two types.

In the first type of technology, reaction and distillation proceed simultaneously in the same physical space, as disclosed, for example, in International patent application WO-A-90/02 603, U.S. Pat. No. 4,471,154, U.S. Pat. No. 4,475,005, U.S. Pat. No. 4,215,011, U.S. Pat. No. 4,307,254, U.S. Pat. No. 4,336,407, U.S. Pat. No. 4,439,350, U.S. Pat. No. 5,189,001, U.S. Pat. No. 5,266,546, U.S. Pat. No. 5,073,236, U.S. Pat. No. 5,215,011, U.S. Pat. No. 5,275,790, U.S. Pat. No. 5,338,517, U.S. Pat. No. 5,308,592, U.S. Pat. No. 5,236,663, U.S. Pat. No. 5,338,518, also European patents EP-B1-0 008 860, EP-B1-0 448 884, EP-B1-0 396 650 and EP-B1-0 494 550, and in European patent application EP-A1-0 559 511. The catalyst is then generally in contact with a descending liquid phase, generated by the reflux introduced to the top of the distillation zone, and with an ascending vapour phase, generated by the reboil vapour introduced into the bottom of the zone. In this type of technology, the gaseous stream containing the hydrogen necessary for the reaction zone for carrying out the process of the invention can be added to the vapour phase, preferably substantially at the inlet of at least one catalytic bed in the reaction zone.

In the second type of technology, the catalyst is located such that the reaction and distillation generally proceed independently and consecutively, as disclosed, for example, in U.S. Pat. No. 4,847,430, U.S. Pat. No. 5,130,102 and U.S. Pat. No. 5,368,691, the vapour from distillation in practice not passing through any catalytic bed in the reaction zone. Thus if this type of technology is used, the process of the invention is generally such that the flow of the liquid to be hydroisomerised is co-current with the flow of the gaseous stream containing hydrogen and such that the distillation vapour is in practice not in contact with the catalyst (which generally means that the vapour is separated from the liquid to be hydroisomerised), for any catalytic bed in the internal portion of the hydroisomerisation zone. Such systems generally comprise at least one means for distributing liquid which can, for example, be a liquid distributor, in each catalytic bed in the reaction zone. Nevertheless, since these technologies were designed for catalytic reactions between liquid reactants, they are not suitable without modification for a catalytic hydroisomerisation reaction where one of the reactants, hydrogen, is a gas.

For each catalytic bed in the internal portion of the hydroisomerisation zone, it is thus generally necessary to add a means for introducing a gaseous stream containing hydrogen, for example using the techniques described below. Thus the internal portion of the hydroisomerisation zone comprises at least one liquid distribution means and at least one means for introducing a gaseous stream into each catalytic bed in the internal portion of the hydroisomerisation zone. In a first technique, the means for introducing a gaseous stream into each catalytic bed is identical to the means for distributing liquid in the catalytic bed, i.e., there is a means for introducing gas into the liquid upstream of the liquid distribution means (with respect to the direction of circulation of the liquid). In practice, and in everyday terms, this amounts to the gas being bubbled into the liquid upstream of the liquid distribution means. In a further technique, the means for introducing a gas stream is located substantially at the level of the liquid distribution means, below or in it, preferably close to the liquid distribution means of the catalytic bed, i.e., the gas and liquid are separately introduced into the catalytic bed.

Thus when the hydroisomerisation zone associated with the distillation zone is at least partially internal to the distillation zone, in one preferred embodiment of the process of the invention, the catalyst in the internal portion of the hydroisomerisation zone is located in that portion in accordance with the basic process described in U.S. Pat. No. 5,368,691, arranged such that each catalytic bed in the internal portion of the hydroisomerisation zone is supplied with a gaseous stream containing hydrogen, regularly distributed at its base, for example using one of the three techniques described above. In this technology, in which the distillation zone comprises a single column and in which the hydroisomerisation zone is completely internal to the column (which differs from the process of the invention), the catalyst comprised in each catalytic bed internal to the distillation zone is then in contact with an ascending liquid phase, generated by the reflux introduced to the head of the distillation column, and with the gaseous stream containing hydrogen which circulates in the same direction as the liquid; contact with the vapour phase in the distillation step is avoided by passing the latter via at least one specially provided chimney.

When the hydroisomerisation zone associated with the distillation zone is at least partially internal to the distillation zone, the operating conditions in the internal portion are connected to the operating conditions for the distillation step. Distillation is generally carried out so as to minimise the quantity of isobutene in the bottom product and thus maximise the isobutene yield of the process and to minimise the quantity of butene-2 compounds and butene-1 in the overhead product, in order to produce high purity isobutene overhead. It is carried out at a pressure which is generally in the range 2 to 30 bars, preferably in the range 4 to 15 bars, more preferably in the range 4 to 10 bars (1 bar=$10^5$ Pa), with a reflux ratio in the range 1 to 30, preferably in the range 5 to 20. The overhead temperature in the distillation zone is generally in the range 0° C. to 200° C. and the temperature at the bottom of the distillation zone is generally in the range 5° C. to 250° C. The temperatures in the distillation zone can be calculated from the pressures, as is known to the skilled person. The hydroisomerisation reaction is carried out under conditions which are more generally intermediate those at the head and bottom of the distillation zone, at a temperature in the range 20° C. to 150° C., and preferably in the range 40° C. to 80° C., and at a pressure in the range 2 to 30 bar, preferably in the range 4 to 15 bar, and more preferably in the range 4 to 10 bar. The liquid which undergoes hydroisomerisation is supplied with a gaseous stream containing hydrogen, preferably as the major portion.

In a second implementation of the process of the invention, the hydroisomerisation reaction zone is completely internal to the distillation zone.

More generally, the catalyst used in each hydroisomerisation zone in the process of the present invention generally comprises at least one metal selected from the group formed by noble metals from group VIII of the periodic table and nickel, i.e., selected from the group formed by ruthenium, rhodium, palladium, osmium, iridium, and platinum, preferably palladium, or nickel, used as it is or, as is preferable, deposited on a support. At least 50% by weight of the total amount of metal must generally be in its reduced form. The quantity of noble metal in the catalyst is generally about 0.01% to about 2% by weight. When nickel is used, the proportion of nickel with respect to the total weight of the catalyst is in the range 5% to 70%, preferably in the range 10% to 70%, and generally a catalyst is used in which the average nickel crystallite size is less than 10 nm, preferably less than 8 nm, and more preferably less than 6 nm. However, any other hydroisomerisation catalyst which is known to the skilled person can also be used. The catalyst is normally treated with a sulphur compound then with hydrogen before use. The catalyst is generally sulphurised in situ or ex situ so that the sulphur is chemisorbed on at least a portion of the metal. The chemisorbed sulphur encourages the hydroisomerisation reaction of butene-1 to butene-2 compounds over the isobutene hydrogenation reaction and thus maximises the isobutene yield from the process.

The hydroisomerisation catalyst support is generally selected from the group formed by alumina, silica-aluminas, silica, zeolites, activated charcoal, clays, aluminous cements, rare earth oxides and alkaline-earth oxides, used alone or as a mixture. A support based on alumina or silica is preferably used, with a specific surface area in the range 10 to 300 m$^2$/g, preferably in the range 30 to 70 m$^2$/g.

Non limiting examples of commercially available catalysts which can be used in the present invention are those sold by Catalysts and Chemicals under reference number C-31, by Girdler Corporation under reference G-55 or, as is preferable, by Procatalyse under references LD-265, LD-265S, LD-267 and LD-267R.

The major portion of the bottom effluent from the distillation zone, which generally contains principally butene-2 compounds and normally normal-butane, is treated in a distillation zone, preferably an extractive distillation zone. The normal-butane which is generally in this effluent principally originates from the feed to the process of the invention and a small amount may be generated in the hydroisomerisation zones by hydrogenation of the butenes. The distillation zone produces a first effluent, from the bottom in the case of extractive distillation, comprising butene-2 compounds as its major portion and practically no normal-butane, and a second effluent comprising normal-butane as its major portion and practically no butene-2 compounds. The major portion of the first effluent is sent as a feed to the skeletal isomerisation zone of the process. Adding a means for separating the butene-2 compounds from normal-butane upstream of the skeletal isomerisation zone of the process when the feed contains normal-butane can substantially reduce the quantity of normal-butane which is passed into the skeletal isomerisation zone of the process; this means that the capacity of the skeletal isomerisation zone of the process of the invention can be reduced. The advantage of using extractive distillation over any other means for separating these two compounds, such as conventional distillation, arises from the fact that the difference between the boiling points of normal-butane and butene-2 compounds is small and thus, for the same separation, normal distillation would require many more theoretical plates and incur a higher costs.

In a preferred implementation of the process of the invention, the second distillation zone is an extractive distillation zone. Extractive distillation is carried out in the presence of a non aqueous solvent which is selective for olefinic hydrocarbons, at least part of which is introduced into a first portion of the extractive distillation zone, to recover an overhead fraction which is rich in normal-butane, constituting a major portion of the second effluent in the extractive distillation zone, and a tail fraction which is treated in a second portion of the extractive distillation zone, to recover overhead at least part of a distillate which is rich in olefinic hydrocarbons, which distillate principally constitutes the first effluent of the extractive distillation zone, and a tail residue containing essentially solvent. The solvent is generally a solvent which has a substantial selectivity for olefins. In particular, it can be selected from the group formed by N,N-dimethylformamide, N,N-diethylformamide, N,N-dimethylacetamide, formylmorpholine, N-methylpyrrolidone, butyrolactone and furfural.

In the skeletal isomerisation zone of the process of the invention, part of the linear butenes present in the first effluent from the bottom of the distillation zone, preferably the major part, is isomerised to isobutene. The effluent from the skeletal isomerisation zone of the process of the invention thus contains isobutene formed during reaction of the linear butenes. Part of the effluent from the skeletal isomerisation zone, preferably the major part, is then re-injected upstream of the distillation zone to separate the isobutene formed from the linear butenes. The quantity of supplemental isobutene formed in the skeletal isomerisation zone can not, of course, be higher than the quantity of linear butenes already present in the initial process feed. Given that part of the effluent from the skeletal isomerisation zone of the process of the invention, preferably the major part, is recycled upstream of the distillation zone of the process of the invention, the flow rate in the skeletal isomerisation zone of the process can be varied. The higher the flow rate through the skeletal isomerisation zone of the process, the higher the supplemental quantity of isobutene formed in the skeletal isomerisation zone and thus the higher the total isobutene yield. The major portion of the effluent from the skeletal isomerisation zone is recycled upstream of the process of the invention, as a partial feed to the distillation zone or, as is preferable, as a partial feed for the first hydroisomerisation zone in the preferred case when such is present.

The skeletal isomerisation zone generally functions under the operating conditions given below, which are known to the skilled person, and depend on whether the catalyst includes a zeolite or not.

When the skeletal isomerisation catalyst includes a zeolite, the feed in the skeletal isomerisation zone is brought into contact with the skeletal isomerisation catalyst at a temperature which is in the range 150° C. to 500° C., preferably in the range 150° C. to 450° C., and at a pressure which is in the range 0.01 to 1, preferably in the range 0.01 to 0.5 MPa absolute. The space velocity is in the range 0.1 to 10, preferably in the range 0.5 to 6 h$^{-1}$, expressed as the volume of olefinic feed per volume of catalyst per hour. The catalyst thus generally includes between 5% and 100%, preferably 10% to 90%, and more preferably 20% to 80% by weight, of molecular sieve (or zeolite), the complement to 100% by weight being formed by the matrix. The molecular sieve is preferably selected from the group formed by the following sieves: SAPO-31, SAPO-11, theta-1, EU-1, omega, mordenite, ferrierite, Nu-10, Nu-86 and Nu-87, and the matrix is alumina.

When the skeletal isomerisation catalyst does not include a zeolite, the catalyst contains principally alumina (generally eta and/or gamma) possibly with at least one additive such as those based on titanium and/or a group IIIA element, usually having undergone prior steam treatment (see, for example, U.S. Pat. No. 3,558,733, U.S. Pat. No. 2,417,647, U.S. Pat. No. 4,013,590, U.S. Pat. No. 4,038,337, U.S. Pat. No. 4,434,315 or U.S. Pat. No. 5,321,195 or United Kingdom patent application GB-A-2 129 701 or EP-A-0 696 265). The process is carried out at a temperature which is in the range 300° C. to 570° C., preferably in the range 400° C. to 550° C., a pressure which is in the range 0.1 to 1 MPa, preferably in the range 0.1 to 0.5 MPa, at a space velocity in the range 0.1 to 10 h$^{-1}$, preferably in the range 0.5 to 6 h$^{-1}$, with the molar ratio of water injected to olefinic hydrocarbons being in the range 0.1 to 10, preferably in the range 0.5 to 3. The process is described in patent application EP-A-0 611 185, for example.

Since certain compounds can be present in the feed which are inert as regards the reactions occurring in the process and certain by-products can be formed during one or another of the steps of the process, and given that part, preferably a major part, of the effluent from the skeletal isomerisation zone is recycled upstream of the distillation zone, it may be necessary to provide for at least one purge in order to prevent accumulation of such compounds in the process. As an example, a purge may be provided upstream of the skeletal isomerisation zone of the process in order to avoid an accumulation of normal-butane if present in the process feed. It is also possible to place in the effluent from the skeletal isomerisation zone of the process, a means (for example distillation) for eliminating compounds which are lighter than the $C_4$ hydrocarbons which should be formed in this part of the process, and a means (for example distillation) for eliminating compounds which are heavier than the $C_4$ hydrocarbons which could have formed in this portion of the process.

EXAMPLES

Pilot hydroisomerisation tests were carried out starting from an olefinic $C_4$ feed using a LD267R hydroisomerisation catalyst, produced and sold by Procatalyse, which packed each catalytic bed. The results of these tests are shown in Table 1 below: they allowed process engineering parameters to be calculated which allowed the process of the invention to be simulated using suitable software. The software used for this simulation is sold by SIMCI under the name Pro2.

TABLE 1

| PILOT TEST RESULTS | | | | | | | | | |
|---|---|---|---|---|---|---|---|---|---|
| T ° C. | | 40 | 60 | 90 | 50 | 50 | 50 | 50 | 50 |
| HSV h$^{-1}$ | | 30 | 30 | 30 | 30 | 30 | 30 | 30 | 30 |
| P bars | | 10 | 10 | 10 | 6.5 | 10 | 15 | 10 | 10 |
| H$_2$/HC m/m | | 0.17 | 0.17 | 0.17 | 0.17 | 0.17 | 0.17 | 0.1 | 0.19 |
| | fd | eff | eff | eff | eff | eff | eff | eff | eff |
| <C$_4$ | | 0.11 | 0.12 | 0.11 | 0.1 | 0.10 | 0.10 | 0.10 | 0.11 |
| iC$_4$ | | 5.75 | 5.75 | 5.73 | 5.71 | 5.76 | 5.75 | 5.72 | 5.76 |
| iC$_4^=$ | | 78.72 | 78.71 | 78.73 | 78.77 | 78.73 | 78.73 | 78.75 | 78.71 |
| 1-C$_4^=$ | | 1.30 | 0.91 | 0.75 | 1.15 | 1.01 | 1.18 | 1.13 | 1.00 |
| n-C$_4$ | | 7.19 | 7.17 | 7.14 | 7.14 | 7.18 | 7.19 | 7.16 | 7.20 |
| tr2-C$_4^=$ | | 5.40 | 5.48 | 5.40 | 5.46 | 5.49 | 5.41 | 5.46 | 5.48 |
| cs2-C$_4^=$ | | 1.54 | 1.85 | 2.14 | 1.66 | 1.74 | 1.64 | 1.69 | 1.75 | where fd = feed and eff = effluent, and the following legend for the above table and following tables:
<C$_4$: compounds containing less than 4 (4 excluded) carbon atoms per molecule (or C3$^-$);
iC$_4$: isobutane;
iC$_4^=$: isobutene;
1-C$_4^=$: butene-1;
C$_4^{==}$1,3: 1,3-butadiene;
nC$_4$: normal-butane;
tr2-C$_4^=$: trans-butene-2;
cs2-C$_4^=$: cis-butene-2;
>C$_4$: compounds containing more than 4 (4 excluded) carbon atoms per molecule (or C5$^+$).

Figure 2:
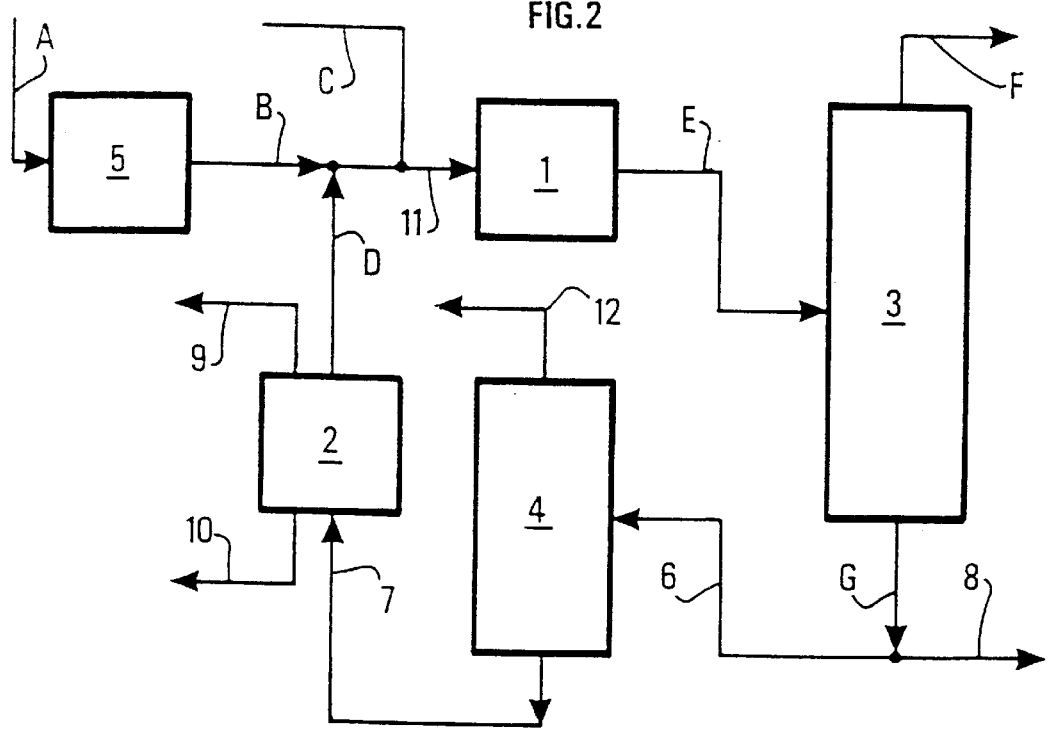

FIGS. 1 and 2 are block flow sheets of the process described in Examples 1 and 2 respectively.

Two examples simulated by the process engineering were carried out. They are described below. In these two examples, the skeletal isomerisation zone was modelled so that the butenes were substantially at thermodynamic equilibrium at the reaction temperature, which was generally 490° C. to 500° C.

Example 1

Example 1 was carried out following the diagram shown in FIG. 1. 1-raffinate was introduced via a line (A) then via a line (11) into a hydroisomerisation zone (1), mixed with effluent (B) from the skeletal isomerisation zone (2). The effluent from zone (1) was sent via a line (C) to a reactive distillation zone (3). The head product from distillation zone (D) principally comprised pure isobutene. Part of the bottom product from distillation zone (E) was introduced via a line (6) into extractive distillation zone (4), the effluent (7) from zone (4) acting as a feed for zone (2). Possible purges are represented by lines (8), (9), (10) and (12).

The configuration of the reactive distillation unit, comprising three hydroisomerisation zones located external to the column, was as follows:

column with 130 theoretical plates, numbered from top to bottom;
supply to plate n° 90;
the external reactors were supplied by draw-offs located at plates 10, 25 and 39 respectively. The effluent from each of these external reactors was re-introduced to the draw-off plate supplying the external reactor under consideration.

Reactors:

The three reactors each contained 10 tonnes of catalyst.

Operating conditions:

Reflux ratio: 20;
Column head pressure: 6.2 bars absolute;
Column bottom pressure: 7 bars absolute;
Temperature of column supply: 59° C.;
Column head temperature: 45° C.;
Column bottom temperature: 72° C.;
Temperature of reactor supplied by draw-off from plate 10: 53° C.;
Pressure of reactor supplied by draw-off from plate 10: 6.6 bars absolute;
Flow rate in reactor supplied by draw-off from plate 10: 5200 kmole/h;
Temperature of reactor supplied by draw-off from plate 25: 53.5° C.;
Pressure of reactor supplied by draw-off from plate 25: 6.6 bars absolute;
Flow rate in reactor supplied by draw-off from plate 25: 5200 kmole/h;
Temperature of reactor supplied by draw-off from plate 39: 54° C.;
Pressure of reactor supplied by draw-off from plate 39: 6.7 bars absolute;
Flow rate in reactor supplied by draw-off from plate 39: 5200 kmole/h.

With this configuration and under these operating conditions, the simulation led to the following results:

| | A (wt %) | B (wt %) | C (wt %) | D (wt %) | E (wt %) |
|---|---|---|---|---|---|
| $<C_4$ | 0.10 | 2.59 | 1.54 | 5.05 | — |
| $iC_4$ | 1.88 | 0 | 0.92 | 3.38 | — |
| $iC_4^=$ | 37.13 | 21.86 | 28.34 | 91.46 | 0.57 |
| $nC_4^=1$ | 27.72 | 12.09 | 7.31 | 0.04 | 0.38 |
| $C_4^=1,3$ | 0.99 | — | — | — | — |
| $nC_4$ | 16.93 | 1.59 | 8.85 | 0.02 | 0.73 |
| $tr2\text{-}C_4^=$ | 6.74 | 15.02 | 18.74 | 0.03 | 38.33 |
| $cs2\text{-}C_4^=$ | 8.42 | 12.09 | 14.18 | — | 27.06 |
| $>C_4$ | 0.10 | 34.75 | 20.12 | — | 32.94 |
| Total (kt/yr) | 150 | 205 | 355 | 108 | 217 |

A: Feed for first hydroisomerisation unit;
B: Effluent from skeletal isomerisation unit mixed with stream A upstream of first hydroisomerisation unit;
C: Effluent from first hydroisomerisation unit; this stream was also the feed for the reactive distillation step;
D: Effluent from head of reactive distillation;
E: Effluent from bottom of reactive distillation.

Total isobutene yield with respect to isobutene in feed: 177%
Isobutene yield with respect to iso and normal butenes and butadiene: 82%
Butene-1 in isobutene at column head: $4.5 \times 10^{-4}$.

Example 2

Example 2 was carried out following the diagram shown in FIG. 2. A $C_4$ feed from steam cracking was introduced via a line (A) into a hydrogenation zone (5). The effluent from zone (5) was introduced via line (B) then via line (11) into hydroisomerisation zone (1) mixed with 1-raffinate from line (C) and with effluent (D) from skeletal isomerisation zone (2). The effluent from zone (1) was sent via a line (E) to a reactive distillation zone (3). The head product from distillation zone (D) principally comprised pure isobutene. Part of the bottom product (G) from distillation zone was introduced into extractive distillation zone (4) via a line (6), effluent (7) from zone (4) acting as the feed for zone (2). Possible purges are represented by lines (8), (9), (10) and (12).

The configuration of the reactive distillation unit, comprising three hydroisomerisation zones located external to the column, was as follows:
column with 130 theoretical plates;
supply to plate n° 90;
the external reactors were supplied by draw-offs located at plates 10, 25 and 39 respectively. The effluent from each of these external reactors was re-introduced to the draw-off plate supplying the external reactor under consideration.

Reactors:
The three reactors each contained 10 tonnes of catalyst.
Operating Conditions:
Reflux ratio: 20;
Column head pressure: 6.2 bars absolute;
Column bottom pressure: 7 bars absolute;
Temperature of column supply: 59° C.;
Column head temperature: 44° 0C.;
Column bottom temperature: 72.5° C.;
Temperature of reactor supplied by draw-off from plate 10: 53° C.;
Pressure of reactor supplied by draw-off from plate 10: 6.6 bars absolute;
Flow rate in reactor supplied by draw-off from plate 10: 5200 kmole/h;
Temperature of reactor supplied by draw-off from plate 25: 53.5° C.;
Pressure of reactor supplied by draw-off from plate 25: 6.6 bars absolute;
Flow rate in reactor supplied by draw-off from plate 25: 5200 kmole/h;
Temperature of reactor supplied by draw-off from plate 39: 54° C.;
Pressure of reactor supplied by draw-off from plate 39: 6.7 bars absolute;
Flow rate in reactor supplied by draw-off from plate 39: 5200 kmole/h.

With this configuration and under these operating conditions, the simulation led to the following results:

| | A (wt %) | B (wt %) | C (wt %) | D (wt %) | E (wt %) | F (wt %) | G (wt %) |
|---|---|---|---|---|---|---|---|
| $<C_4$ | 0.05 | 0.05 | 0.10 | 2.61 | 1.71 | 6.59 | 0.00 |
| $iC_4$ | 0.95 | 1.95 | 1.88 | 0.00 | 0.77 | 3.37 | 0.00 |
| $iC_4^=$ | 18.74 | 17.74 | 37.13 | 22.05 | 23.86 | 89.99 | 0.54 |
| $nC_4^=1$ | 13.99 | 28.99 | 27.72 | 12.20 | 2.91 | 0.02 | 0.16 |
| $C_4^=1,3$ | 50.01 | 1.00 | 0.99 | 0.00 | 0.00 | 0.00 | 0.00 |
| $nC_4$ | 8.55 | 9.56 | 16.93 | 1.31 | 6.05 | 0.01 | 0.44 |
| $tr2\text{-}C_4^=$ | 3.40 | 27.41 | 6.74 | 15.15 | 25.73 | 0.01 | 40.40 |

-continued

|  | A (wt %) | B (wt %) | C (wt %) | D (wt %) | E (wt %) | F (wt %) | G (wt %) |
|---|---|---|---|---|---|---|---|
| cs2-C$_4$$^=$ | 4.25 | 13.25 | 8.42 | 12.20 | 16.68 | 0.00 | 25.80 |
| >C$_4$ | 0.05 | 0.05 | 0.10 | 34.47 | 22.29 | 0.00 | 32.65 |
| Total (kt/yr) | 75 | 75 | 75 | 273 | 423 | 110 | 273 |

A: Feed to butadiene selective hydrogenation unit;
B: Effluent from butadiene selective hydrogenation unit;
C: Complement of feed mixed with stream B and stream D upstream of first hydroisomerisation unit (this feed is 1-raffinate type);
D: Effluent from skeletal isomerisation unit mixed with stream B and C upstream of first hydroisomerisation unit;
E: Effluent from first selective hydroisomerisation unit; this stream is also the reactive distillation feed;
F: Effluent from head of reactive distillation;
G: Effluent from bottom of reactive distillation.

Total isobutene yield with respect to isobutene in feed: 236%
Isobutene yield with respect to iso and normal-butenes and butadiene: 78%
Butene-1 in isobutene at column head: $2 \times 10^{-4}$.

Thus the two examples of embodiments of the process of the invention showed the value of combining different reaction and distillation zones, which resulted in an exceptional yield of pure isobutene produced compared to the isobutene present in the feed from the first hydroisomerisation unit.

We claim:

1. A process comprising treating a feed, the major portion comprising olefinic hydrocarbons containing 4 atoms per molecule, including isobutene, also butene-1 and butene-2 compounds in a ratio which substantially corresponds to the thermodynamic equilibrium, in which said feed is treated in a first distillation zone, associated with at least one hydroisomerisation reaction zone, so as to produce an overhead effluent from the distillation zone which is rich in isobutene, and a bottom effluent from the distillation zone which is rich in butene-2 compounds, the major portion of the bottom effluent being sent to a second distillation zone, which produces a first effluent comprising butene-2 compounds as its major portion and a second effluent comprising normal-butane as its major portion, the major portion of said first effluent being passed into a skeletal isomerisation zone, and a portion of the first effluent from the skeletal isomerisation zone being recycled upstream of the first distillation zone.

2. A process according to claim 1, in which the major portion of the effluent from the skeletal isomerisation zone is recycled upstream of the first distillation zone.

3. A process according to claim 1, in which the feed is obtained by treating, in a first hydroisomerisation zone, a cut comprising as its major portion olefinic hydrocarbons containing 4 atoms per molecule, the major portion of the effluent from said first hydroisomerisation zone then acting as the feed which is supplied to the first distillation zone.

4. A process according to claim 3, in which said portion of effluent from the skeletal isomerisation zone is recycled upstream of the first hydroismerisation zone.

5. A process according to claim 1, in which the hydroisomerisation zone associated with the first distillation zone is completely internal to said distillation zone.

6. A process according to claim 1, in which the hydroisomerisation zone associated with the first distillation zone is completely external of said distillation zone.

7. A process according to claim 1, in which the hydroisomerisation zone associated with the first distillation zone is both internal to and external of said distillation zone.

8. A process according to claim 1, in which each hydroisomerisation zone in the process of the invention is such that the hydroisomerisation reaction is carried out in the presence of a hydroisomerisation catalyst and a gaseous stream containing hydrogen.

9. A process according to claim 8, in which the hydroisomerisation catalyst is a supported catalyst comprising at least one noble metal from group VIII selected from the group consisting of ruthenium, rhodium, palladium, osmium, iridium and platinum, and nickel, treated by a compound containing sulphur then by hydrogen before use.

10. A process according to claim 1, in which the second distillation zone is an extractive distillation zone.

11. A process according to claim 10, wherein the extractive distillation is conducted with a non-aqueous solvent selective for olefin hydrocarbons.

12. A process according to claim 11, wherein said solvent is N$_1$N-dimethylformanide, N$_1$N-dimethylformanide, N$_1$N-dimethylacetamide, formylmorpholine, N-methylpyrrolidone, butyrolactone or furfural.

13. A process according to claim 1, further comprising subjecting the feed to a first hydrosimerization zone and directly passing and effluent from said first hydroisomerization zone to said first distillation zone.

14. A process according to claim 13, wherein said portion of the first effluent kfrom the skeletal isomerization zone is recycled to said first hydroisomerization zone.

15. A process according to claim 1 further comprising providing a feed from steam cracking and passing said feed into hydrogenation zone, and then treating the resultant feed in accordance with the steps of claim 1.

* * * * *